(12) United States Patent
Metelski (10) Patent No.: US 7,158,292 B2
(45) Date of Patent: Jan. 2, 2007

(54) APPARATUS FOR RETAINING AN OPTICAL VIEWING DEVICE

(75) Inventor: Andrzej Metelski, Romanshorn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 54 days.

(21) Appl. No.: 10/322,992

(22) Filed: Dec. 18, 2002

(65) Prior Publication Data

US 2003/0117703 A1 Jun. 26, 2003

(30) Foreign Application Priority Data

Dec. 21, 2001 (DE) ................. 101 63 354

(51) Int. Cl.
*G02B 21/00* (2006.01)
*F16M 13/00* (2006.01)

(52) U.S. Cl. ............... 359/384; 359/382; 248/585; 248/123.11

(58) Field of Classification Search ........... 359/382, 359/384, 368; 248/281.11, 123.11, 123.2, 248/125.2, 585
See application file for complete search history.

(56) References Cited

U.S. PATENT DOCUMENTS

| | | | |
|---|---|---|---|
| 2,656,058 A * | 10/1953 | Foote | 414/550 |
| 3,679,154 A * | 7/1972 | Nichols et al. | 244/17.11 |
| 4,852,842 A | 8/1989 | O'Neill | |
| 5,074,501 A * | 12/1991 | Holtta | 248/118.3 |
| 5,213,293 A * | 5/1993 | Muentener et al. | 248/123.11 |
| 5,288,043 A * | 2/1994 | Tigliev | 248/123.11 |
| 5,484,127 A * | 1/1996 | Mower et al. | 248/284.1 |
| 5,667,186 A * | 9/1997 | Luber et al. | 248/550 |
| 6,038,986 A * | 3/2000 | Ransil et al. | 108/145 |
| 6,628,457 B1 * | 9/2003 | Ito | 359/368 |

FOREIGN PATENT DOCUMENTS

| | | |
|---|---|---|
| DE | 8024962 U1 | 6/1982 |
| EP | 0592703 A1 | 4/1994 |
| EP | 0593791 A1 | 4/1994 |
| EP | 0 866 260 A1 | 2/1998 |
| JP | 10122481 A | 5/1998 |
| WO | WO 99/01693 | 1/1999 |
| WO | WO 0140700 A1 | 6/2001 |
| WO | WO 01/40700 A1 * | 7/2001 |

* cited by examiner

*Primary Examiner*—Mark A. Robinson
*Assistant Examiner*—Lee Fineman
(74) *Attorney, Agent, or Firm*—Hodgson Russ LLP (57) ABSTRACT

An apparatus for retaining an optical viewing device, for example a microscope (8), on a stand having a parallelogram carrier arm (5*a*, 5*b*, 5*c*, 5*d*), comprises an adjustable-length strut (6) acting through a pivot point of the carrier arm and an opposite link of the carrier arm. The strut (6) provides, in different variants, inclination adjustment, and/or vibration damping of the carriers arm.

17 Claims, 6 Drawing Sheets

APPARATUS FOR RETAINING AN OPTICAL VIEWING DEVICE

CROSS REFERENCE TO RELATED APPLICATIONS

This application claims priority of the German patent application 101 63 354.8 filed Dec. 21, 2001 which is incorporated by reference herein.

FIELD OF THE INVENTION

The invention concerns an apparatus for retaining an optical viewing device, for example a microscope, having movable retaining carriers, arranged in parallelogram fashion, with a diagonal support element. The term "support element" is to be understood, for example, as diagonal struts or the like that can transfer forces in a mechanical/geometric arrangement and thus can serve to support or retain, and/or to change the position of, the viewing device. They operate in accordance with lever and/or moment laws, and optionally contain adjustment apparatuses in order thereby to take into account or bring about changed conditions so as to guarantee retention of and/or a change in the position of the viewing device.

BACKGROUND OF THE INVENTION

The apparatus is intended to be usable on a stand foot or on a stand column such as a stand arm, but also on other stands such as ceiling or wall mounts.

Retention of an optical viewing device by means of a stand having a stand arm is necessary in a wide variety of applications, especially in the field of medical technology. These stand arms are often embodied as one-armed carriers which are held in position by means of spring mechanisms and/or lockable brakes, and/or are motor-driven.

WO 99/01693-A presents a stand that is marketed by the Applicant as MS 1. Like previous models as well, it has a carrier arm, constructed as a parallelogram, whose geometrical extension is defined by an obliquely arranged support spring, the support spring serving as weight compensation for the load of the viewing device. In this known assemblage, the spring force is adjustable so that different weights of different or differently equipped viewing devices can be supported or compensated for.

EP 866 260 A discloses a toothed-belt-supported support element that transfers the forces for weight compensation (balance) by means of its geometrical arrangement.

In conventional assemblages, diagonal struts are thus used essentially in order to support specifically arranged carrier arms or carrier arm parts in a desired position, and to direct the stress on those assemblages obliquely into the stand columns. In some circumstances, this task could also be achieved, in the context of these assemblages for performing support functions, if no parallelogram at all were present, but rather the entire assemblage were boom-shaped.

Conventional diagonal struts often also have:

An integrated spring force of a gas spring, as already mentioned above, to compensate for (the weight of) the load.

One or more damping elements, for example gas springs or special rubber bumpers having defined spring and damping characteristics (vibration damping).

Liquid dampers.

The inventor has recognized that the known systems are disadvantageous in the following ways:

a) Insufficient stability in the vertical direction of the microscope (parallel to the optical axis), and thus low positioning accuracy. As a result of poorly controllable vibration stability, unsharp or unstable images can occur with a slow-reacting autofocus system.
b) Heavy construction, in order to achieve improve stability and low-vibration characteristics.
c) Large retention forces are necessary. The elements are thus of solid construction, thereby also (because of the increased weight) resulting in sluggishness and insufficient mobility.

SUMMARY OF THE INVENTION

It is thus the object of the invention to create an apparatus which makes possible stable, vibration-free, and reproducible retention of an optical viewing device and/or which eliminates the disadvantages indicated above. In particular, improved vibration behavior in the vertical direction is to be achieved. The mechanical properties of the assemblage are also intended to result in higher strength for the overall assemblage. The weight of the overall assemblage is intended to be minimized.

This object is achieved by means of an apparatus for retaining an optical viewing device, for example a microscope, on a stand, having at least one support element that braces the stand parts with respect to one another, the support element being arranged or equipped so that in the operating state, a coordination of load-bearing stand parts, in particular the links of a parallelogram-like carrier arm, results. According to the present invention, the bracing support element acts upon the geometrical or physical properties of a parallelogram carrier arm in such a way that the carrier arm becomes distorted or mechanically overrigid.

This inventive idea is not intended to exclude embodiments that can be adjusted in remote-controlled fashion in such a way that the geometry-related force effects, or supporting or damping effects, of the support element are modified as necessary. Similarly, "distortion" and "overrigidity" mean in the context of the invention that the support element could also, within specific but narrow limits, yield in damping fashion or act resiliently.

A controlled and arbitrarily effected distortion of stand parts with respect to one another is critical to achieving the effect according to the present invention.

The term "support element" in the context of the invention also encompasses multiple support elements, e.g. arranged next to one another, that act together.

In an apparatus that is to be used frequently according to the present invention, the support element is inserted approximately diagonally in a carrier arm (parallelogram) comprising four carriers, in which three of the carriers are pivotable relative to the fourth and/or relative to one another.

According to a development of the invention, the support element is modifiable in length in motorized fashion, at least one remotely controllable drive system preferably being provided for the change in length.

The drive system can be arranged outside the support element or also inside it, and can encompass both electrical and pneumatic motors. Spindle drives, telescoping elements, or the like, and their equivalents, are especially encompassed.

A further variant is obtained if the support element is modifiable in length, for example by the user, and is lockable in each length setting, preferably by way of an (in particular, remotely controllable) brake. This can be embodied in such a way that the support element is arranged like an extendable telescoping tube as an approximately diagonal strut in a parallelogram, and in the idle position is locked by a brake that locks the telescoping elements with respect to one another.

For stereotactic operations or presentations in particular, it is advantageous if a motion- and position-sensing unit and a position-memorizing unit, which make possible repeatable positioning at predefined or selected positions, are provided.

A high degree of automation can be achieved if the motion- and position-sensing unit and/or the position memorizing unit comprise at least one processor-based control system and preferably at least one motion- and position-sensing unit for automatic control of the displacement or positioning.

Control systems of this kind can also be utilized in user-specific fashion by the fact that the process control system optionally senses the respective position, inclination, etc. of the carrier and then controls the drive systems so that a specific position is assumed for a specific surgeon. To improve damping behavior, the support element can be equipped with a damping element that is arranged in series or in parallel with the actual support element (e.g. a diagonal strut). According to a development, the invention can also encompass motion, position, angle, or vibration sensors which permit the stand to be used in combination with a control system, or to be integrated into an image-guided surgery (IGS) system and used in computer-controlled fashion.

Particular precision in the use of the invention can be achieved if the support element is retained in zero-clearance fashion in its articulation points and relative to its drive systems.

All the variants mentioned can be combined in any fashion in order to achieve optimum goal-oriented results.

In addition, the following improvements are achieved by using an apparatus according to the present invention as described above:

Good stability with lightweight design.

Little vibration, despite the lightweight design.

In variants having a drive system (with or without brake): definable and controllable inclination angles or vertical positions of the optical viewing device.

In variants having an electronic control system: capability for combination with an autofocus system of the microscope.

Simply designed solution, retrofittable and effective.

Although reference is made in the above text to a surgical microscope, the invention is nevertheless not, limited thereto, but rather is also available to other users of optical devices with retention by means of a stand arm (e.g. projectors, video and photographic cameras, theodolite systems, etc.).

The Parts List and the drawings, together with the subject matter described in the Claims, are an integral constituent of the disclosure of this Application.

BRIEF DESCRIPTION OF THE DRAWINGS

The invention will be presented on the basis of a number of exemplary embodiments with reference to the schematic drawings, in which.

DETAILED DESCRIPTION OF THE INVENTION

Figure 1:
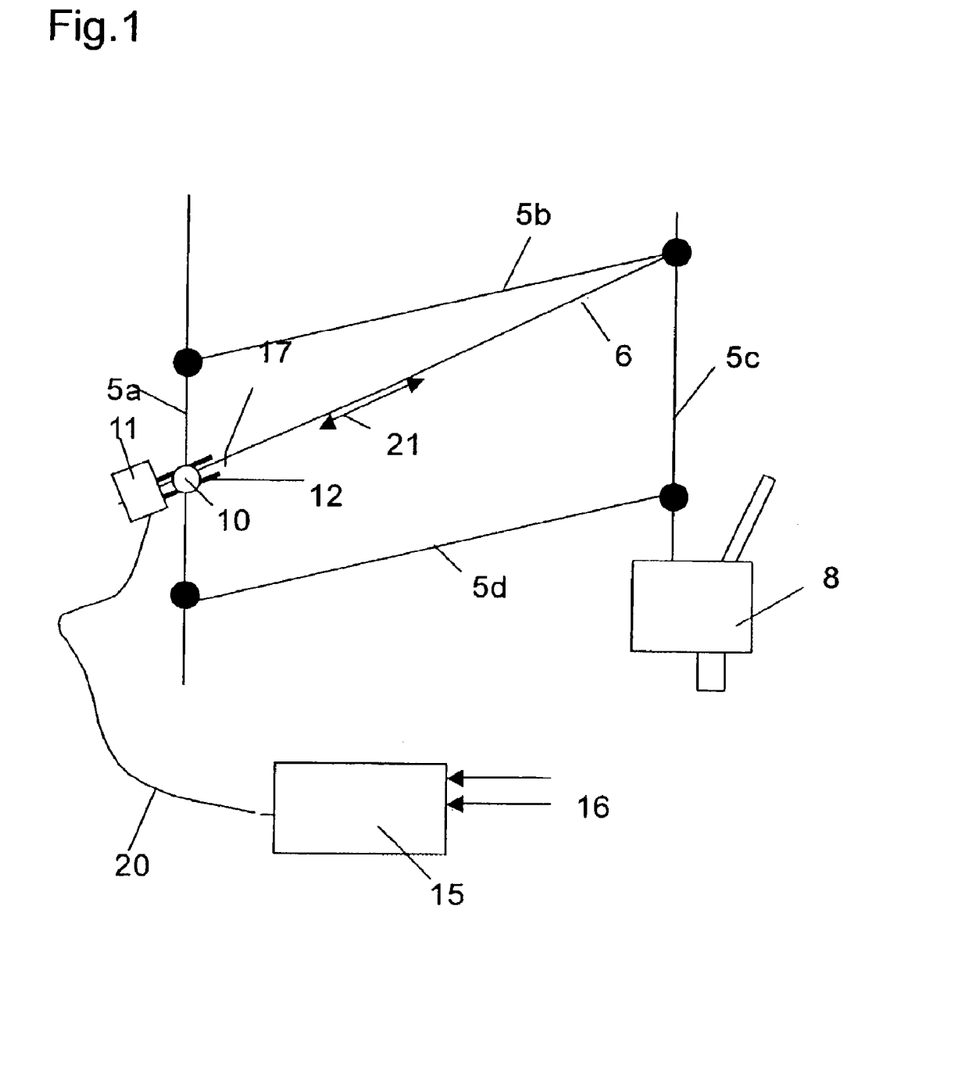
FIG. 1 schematically shows a portion of a conventional stand having a parallelogram carrier with an adjustable-length diagonal strut according to the present invention.

FIG. 1 schematically shows a portion of a conventional stand having a parallelogram carrier 5a–5d and an adjustable-length diagonal strut 6 according to the present invention. Diagonal strut 6 stiffens parallelogram carrier 5a–5d by the fact that it presses by force (preloaded by a motor 11) from carrier 5a into the bearing between carriers 5b and 5c. In the lower region it has a spindle 17 that is rotationally mounted in a thread 12 of a pivoting bearing 10 on retaining carrier 5a. A double arrow 21 indicates the axial force or displacement of diagonal strut 6.

The weight of a microscope 8 is thus supported by parallelogram 5a–5d that is stiffened by means of diagonal strut 6. A control system 15, into which an input 16 can be entered by the user, controls motor 11 via a control line 20.

Figure 4:
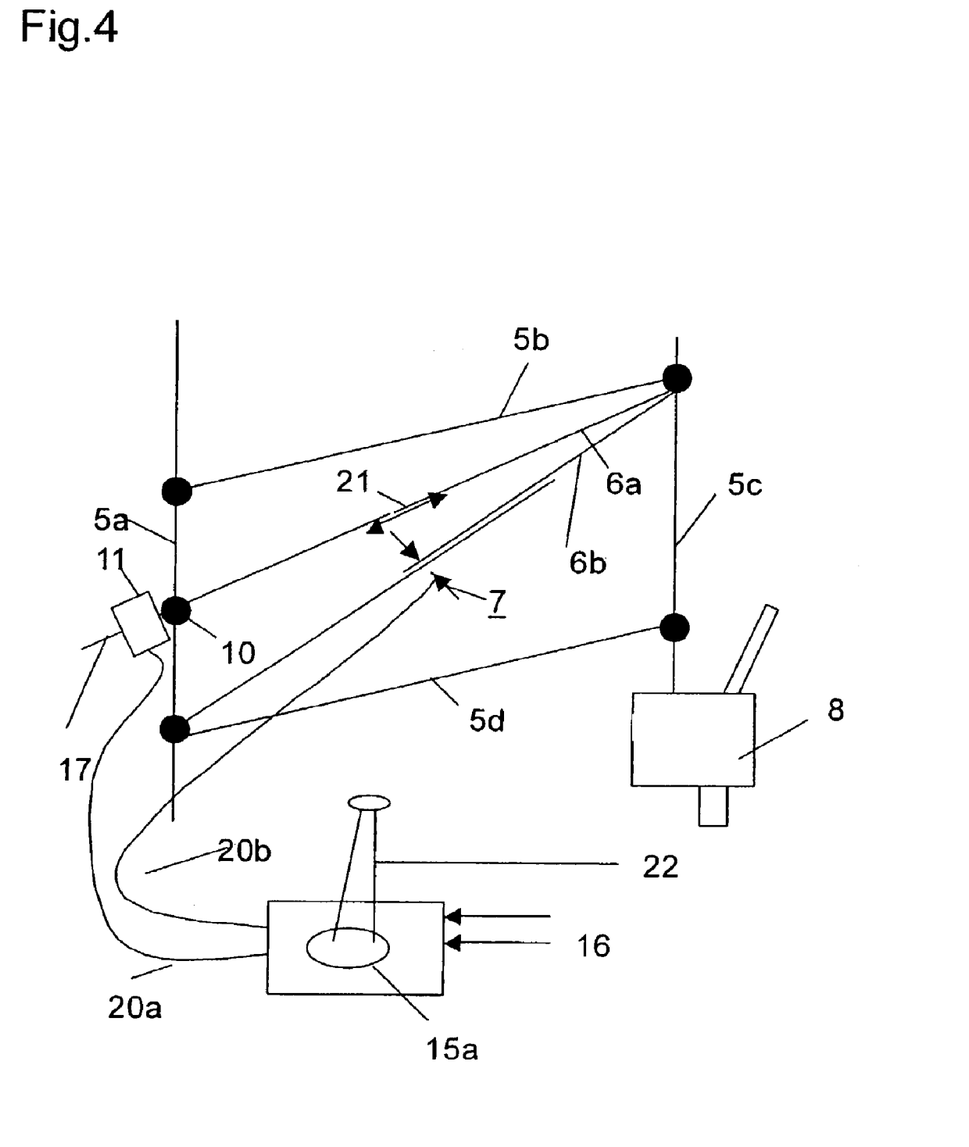
FIG. 4 shows the configuration of FIG. 3 with a motor-driven diagonal strut and a second diagonal strut, acting independently thereof, having a brake for motorized stiffening and a joystick control system for a wide variety of control variants.

As is evident from FIG. 4, a control system 15a of this kind can be combined e.g. with a joystick 22 or the like in order to permit easily operable handling.

Figure 2:
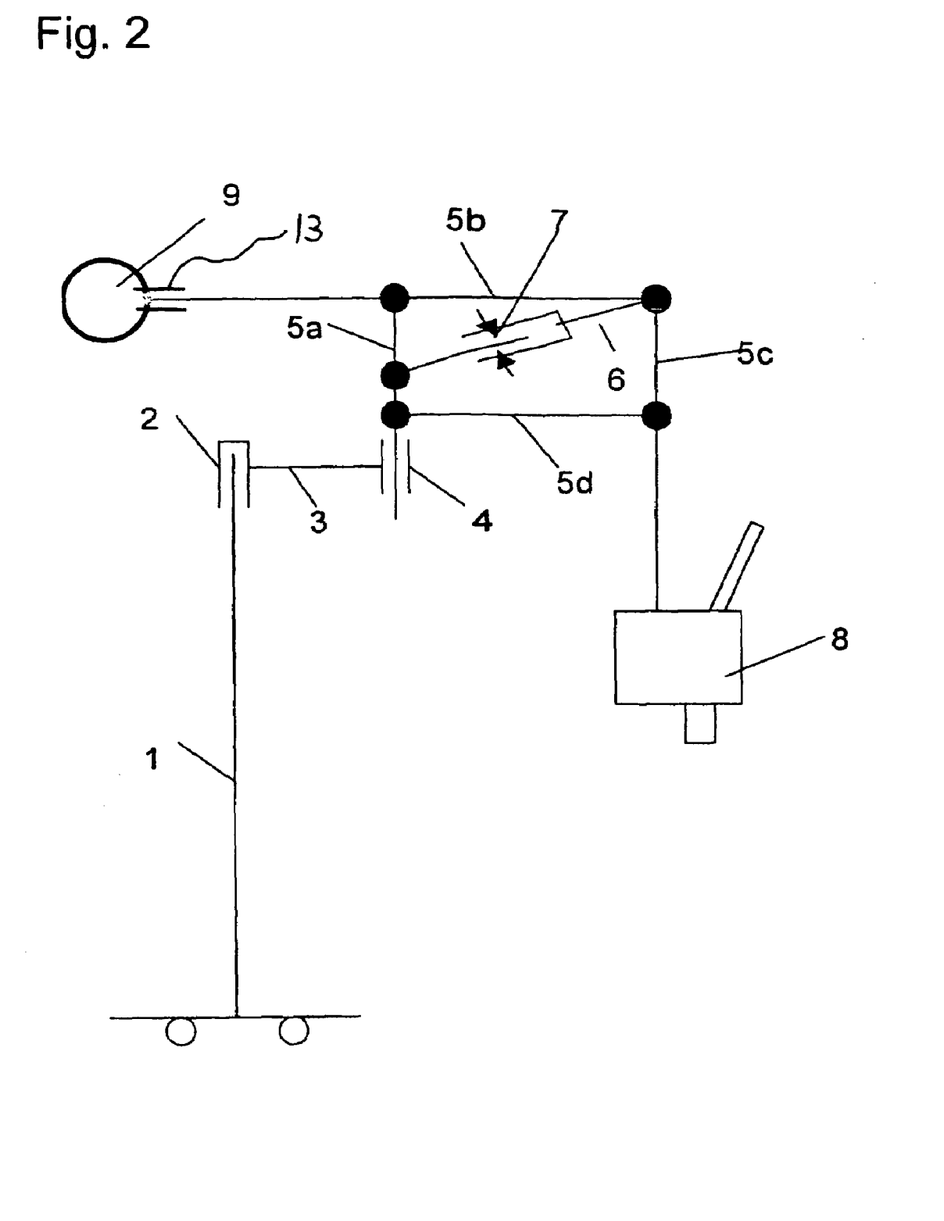
FIG. 2 schematically shows the overall configuration of a stand having a stand arm configured in the manner of a parallelogram with a braked diagonal strut, a counterweight, and a column.

FIG. 2 schematically shows the configuration of a stand for a surgical microscope 8 having a column 1, a rotary joint 2 for a stand arm 3, a rotary joint 4 for the four movable retaining carriers 5a–5d arranged in the manner of a parallelogram, and a diagonal strut 6 according to the present invention having a brake 7 that, in the released state, allows a vertical motion of retaining carrier 5c.

Vertical retaining carrier 5a is not movable in the vertical direction. It is optionally rotatable in bearing 4. In the braked state, raising or lowering of carriers 5b, 5c, and 5d is prevented.

Brake 7 is depicted in only symbolically simplified fashion. In most applications, it will have electrically activated brake pads that brake portions of diagonal strut 6 with respect to one another. A certain frictional effect prior to final braking can intentionally exist so as thereby to achieve frictional damping. This damping process of course is effective only as long as the brake is not applied in the stiffened state of parallelogram 5. Normally, no motion should occur in the stiffened state. In the context of a particular embodiment of the invention, however, in extraordinary load situations a damping effect or an at least slight yielding of diagonal strut 6 could be effective as an overload safety feature.

A counterweight 9 balances, via a bearing 13, the weight of microscope 8 and retaining carriers 5b–d. Brake 7 thus does not have an explicit retaining function but rather only a stiffening function, and optionally a vibration-damping function for the parallelogram.

Figure 3:
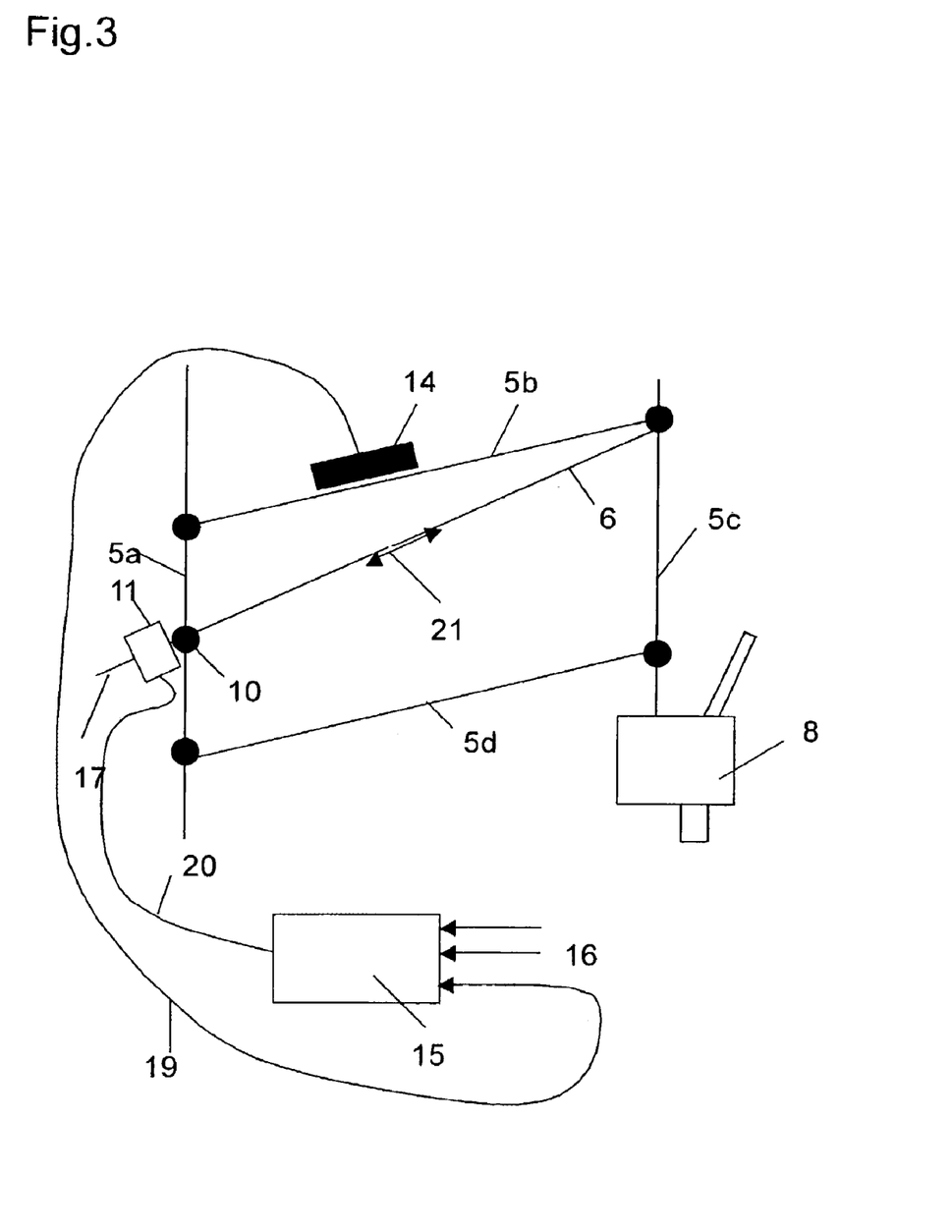
FIG. 3 shows the configuration of FIG. 1 with an adjustable-length diagonal strut and a motion- and position-sensing unit, as well as an electronic activation system for the diagonal strut drive system.

FIG. 3 schematically shows a stand arm according to FIG. 1, but with a motion- and position-sensing unit 14 that is joined to carrier 5b but can also be arranged on the other carriers 5c, 5d, or 6. Motion- and position-sensing unit 14 is depicted only as a symbol, which could also depict multiple motion- and position-sensing units or the like.

Equipped with a suitable program, electronic control unit 15—which is supplied not only with the user's input 16 but also, via a measurement line 19, with information from motion- and position-sensing unit 14—is used to activate motor 11 via control line 20.

Double arrows 21 indicate the ability of diagonal strut 6 to become longer inside parallelogram 5.

The term "motor-driven" is understood to mean assemblages having any desired motorized drive systems, such as electrical, electric-motor, hydraulic, pneumatic, or the like.

Depicted in the configuration shown in FIG. 4 is a "double diagonal strut," symbolically made up of a first diagonal strut 6a and a second diagonal strut 6b, which performs the support function together with first diagonal strut 6a. The two diagonal struts 6a and 6b have different purposes. While the one (6a) has the purpose already described in FIGS. 1 and 3, the other (6b) has approximately the purpose of brake 7 as shown in FIG. 3, so that the two complement one another in terms of effect.

A symbolically depicted joystick 22 allows brake 7 and motor 11 to be controlled via control lines 20a and 20b.

Figure 5:
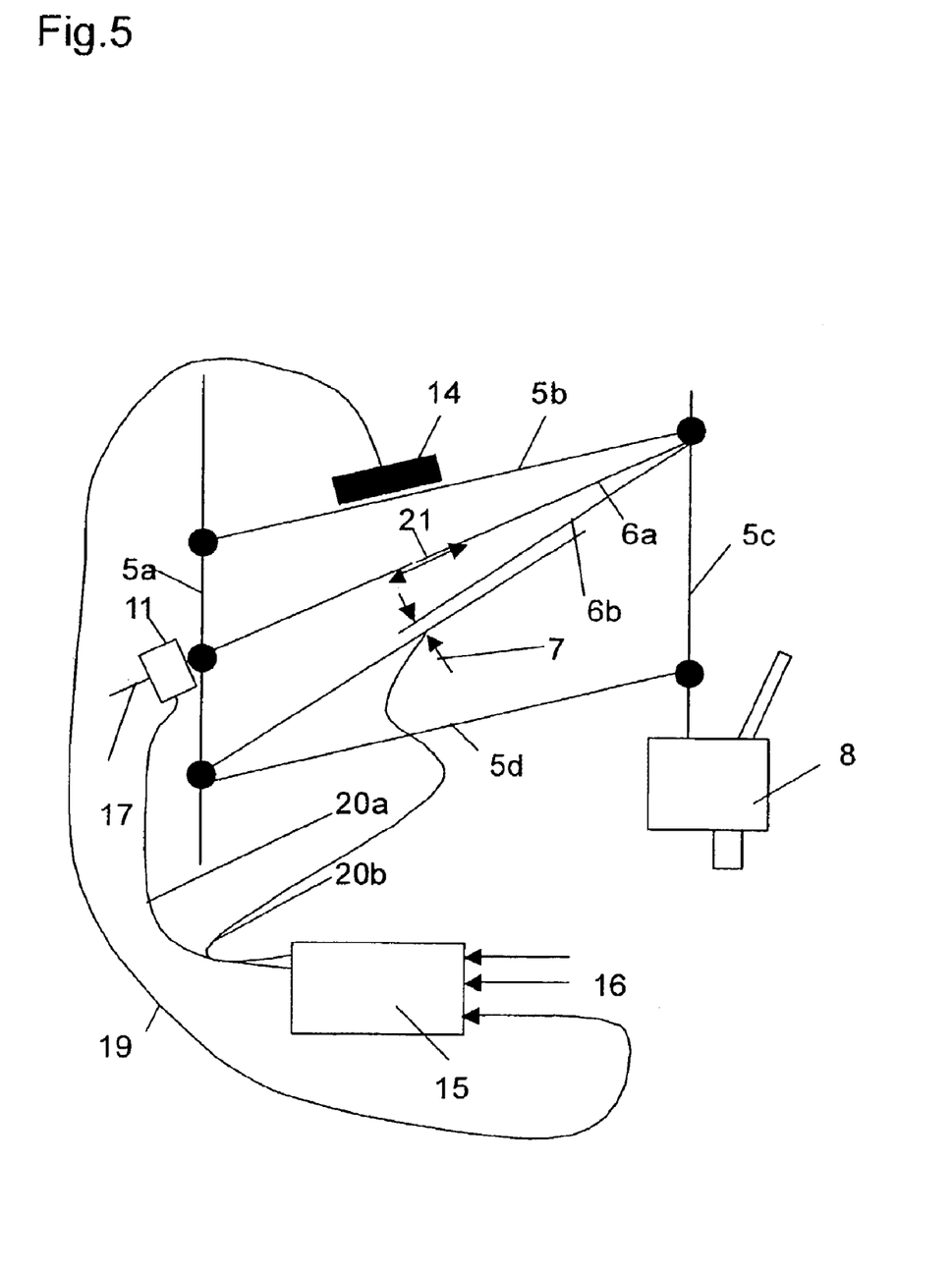
FIG. 5 shows a variant of the configuration according to FIG. 4 with an electronic control system and a motion- and position-sensing unit.

The assemblage shown in FIG. 5 further differs in that a motion- and position-sensing unit 14, which corresponds approximately to motion- and position-sensing unit 14 indicated above and permits automatic positioning of carriers 5b, 5c, and 5d if the program in the control system is equipped accordingly, is additionally provided. Control lines 20a and 20b serve to transmit control information from control system 15 to motor 11 and to brake 7.

Figure 6:
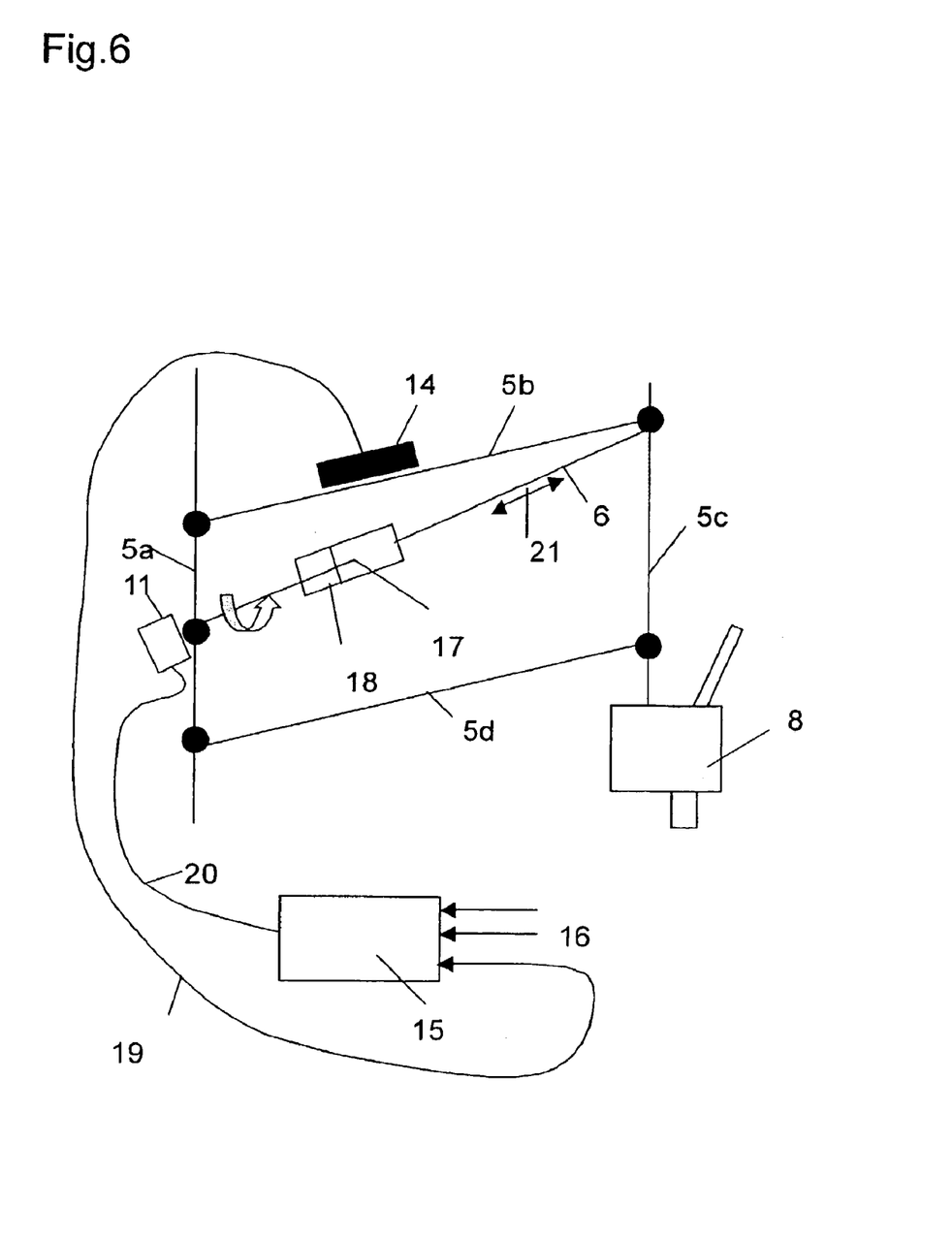
FIG. 6 shows a variant having a spindle inside the parallelogram.

The assemblage according to FIG. 6 shows, as a possible variation, a motor 11 which rotates a spindle 17 that is mounted in a nut 18 on the diagonal strut and thus allows a change in the length of diagonal strut 6.

PARTS LIST

1 Column or stand foot
2 Stand foot rotary joint
3 Stand arm
4 Stand arm rotary joint 5a, b, c, d Movable retaining carriers or carriers or struts, arranged in parallelogram fashion
6 Strut 6a, 6b (support element)
7 Brake
8 Microscope
9 Counterweight
10 Pivoting bearing
11 Motor
12 Thread
13 Bearing
14 Motion- and position-sensing unit for motion and/or vibration and/or position or the like
Control system; 15a Control system with joystick
16 Input signals
17 Spindle
18 Nut
19 Measurement line
20a, b Control line
21 Double arrow
22 Joystick

What is claimed is:

1. An apparatus for retaining an optical viewing device on a stand, the apparatus comprising:
    a parallelogram carrier arm for supporting and positioning the optical viewing device, the carrier arm having four carrier links pivotable relative to one another;
    a brake operable to prevent pivoting of the carrier links relative to one another; and
    a support element that is modifiable in length when the brake is applied to brace the parallelogram carrier arm by applying a force to distort the geometric properties of the carrier arm, wherein the force is independent of a load imposed by the optical viewing device, wherein the support element is a strut arranged to have a line of action extending through a point of pivotal connection between first and second pivotally coupled carrier links and through an intermediate point along a third carrier link, whereby the strut is approximately diagonal with respect to the carrier arm, and wherein the support element is modifiable in length in motorized fashion and the apparatus includes a remotely controllable drive system for changing the length of the support element.

2. The apparatus as defined in claim 1, wherein the drive system is arranged outside the support element and includes a spindle drive.

3. The apparatus as defined in claim 1, wherein the drive system has at least one motor.

4. The apparatus as defined in claim 1, wherein the support element includes a remotely controllable brake for locking the support element in a chosen length setting.

5. The apparatus as defined in claim 4, further comprising a position-sensing unit associated with the carrier arm for providing information indicative of a position of the carrier arm.

6. The apparatus as defined in claim 5, further comprising a motion-sensing unit associated with the carrier arm for providing information indicative of motion of the carrier arm.

7. The apparatus as defined in claim 5, further comprising a control system connected to the position-sensing unit for automatic control of the position of the carrier arm.

8. The apparatus as defined in claim 1, wherein the support element includes a damping element.

9. The apparatus as defined in claim 1, wherein the support element includes a brake element.

10. The apparatus as defined in claim 1, wherein the carrier arm includes a diagonal strut alongside the support element, and the diagonal strut includes a damping element.

11. The apparatus as defined in claim 1, wherein the brake is embodied as a diagonal strut alongside the support element, and the diagonal strut includes a braking element.

12. The apparatus as defined in claim 1, further comprising a motion sensor for sensing motion of the carrier arm.

13. The apparatus according to claim 1, further comprising a position sensor for sensing a position of the carrier arm.

14. The apparatus according to claim 1, further comprising an angle sensor for sensing an angle of the carrier arm.

15. The apparatus according to claim 1, further comprising a vibration sensor for sensing vibration of the carrier arm.

16. The apparatus as defined in claim 1, wherein the support element is retained in zero-clearance fashion in its articulation points and relative to the drive system.

17. A microscope stand comprising:
    a column;
    a stand arm pivotally mounted on the column;

a parallelogram carrier arm adapted to receive and carry a microscope, the carrier arm being pivotally connected to the stand arm and having four carrier links pivotable relative to one another;

a brake operable to prevent pivoting of the carrier links relative to one another; and a support element that is modifiable in length when the brake is applied to brace the parallelogram carrier arm by applying a force to distort the geometric properties of the carrier arm, wherein the force is independent of a load imposed by a microscope, wherein the support element is an adjustable-length strut arranged to have a line of action extending through a point of pivotal connection between first and second pivotally coupled carrier links and through an intermediate point along a third carrier link, whereby the strut is approximately diagonal with respect to the carrier arm approximately diagonal with respect to the carrier arm.

* * * * *